United States Patent [19]
Huff, Jr. et al.

[11] Patent Number: 5,792,894
[45] Date of Patent: Aug. 11, 1998

[54] CONVERSION OF AROMATIC AND OLEFINS

[75] Inventors: George A. Huff, Jr., Naperville; Robert L. Mehlberg, Wheaton; Peter M. Train, Naperville, all of Ill.

[73] Assignee: Amoco Corporation, Chicago, Ill.

[21] Appl. No.: 932,377

[22] Filed: Sep. 7, 1997

Related U.S. Application Data

[63] Continuation of Ser. No. 504,362, Jul. 19, 1995, abandoned.

[51] Int. Cl.[6] .............................. C07C 2/66; C07C 2/70; C07C 2/08
[52] U.S. Cl. .................... 585/446; 585/466; 585/323; 585/529; 585/533; 585/329
[58] Field of Search .............................. 585/446, 466, 585/465, 467, 323, 329, 319, 324, 529, 533

[56] References Cited

U.S. PATENT DOCUMENTS

| | | | |
|---|---|---|---|
| 4,140,622 | 2/1979 | Herout | 208/93 |
| 4,209,383 | 6/1980 | Herout | 208/93 |
| 4,950,823 | 8/1990 | Harandi et al. | 585/322 |
| 5,120,890 | 6/1992 | Sachtler et al. | 585/449 |

FOREIGN PATENT DOCUMENTS

| | | | |
|---|---|---|---|
| 1403329 | 4/1972 | United Kingdom | C07C 3/52 |
| 1525423 | 5/1976 | United Kingdom | C07C 3/52 |
| 2622318 | 5/1976 | United Kingdom | C07C 15/08 |

*Primary Examiner*—Glenn Caldarola
*Assistant Examiner*—Thuan D. Dang
*Attorney, Agent, or Firm*—Frank J. Sroka

[57] ABSTRACT

A process is disclosed for alkylating a volatile aromatic compound with a light aliphatic mono-olefinic alkylating agent and concurrently condensing the alkylating agent in the presence of a solid alkylation- and condensation-promoting catalyst and at a temperature of at least the critical temperature of the reactant mixture and at a total pressure that is above the critical pressure of the reactant mixture.

17 Claims, 2 Drawing Sheets

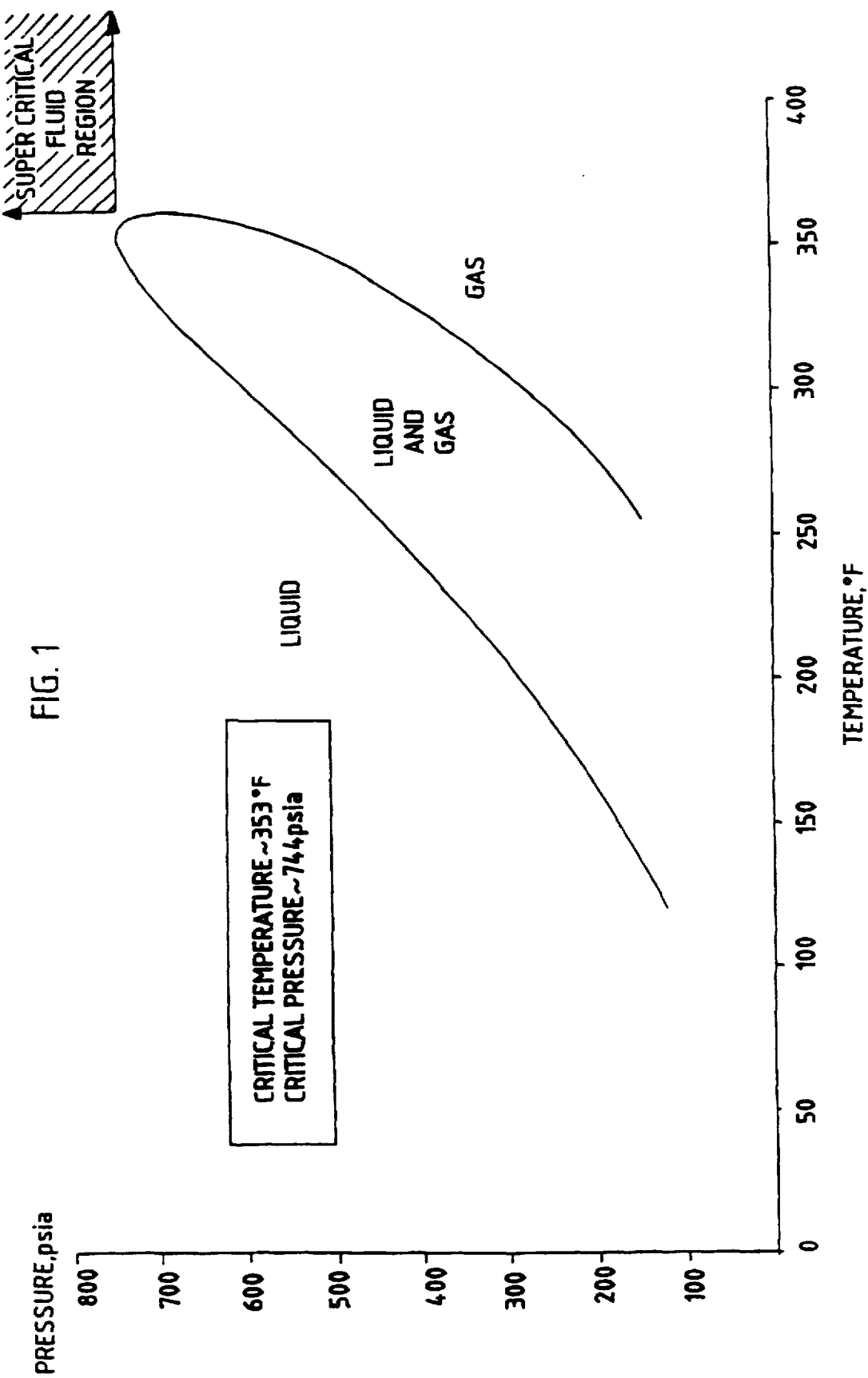

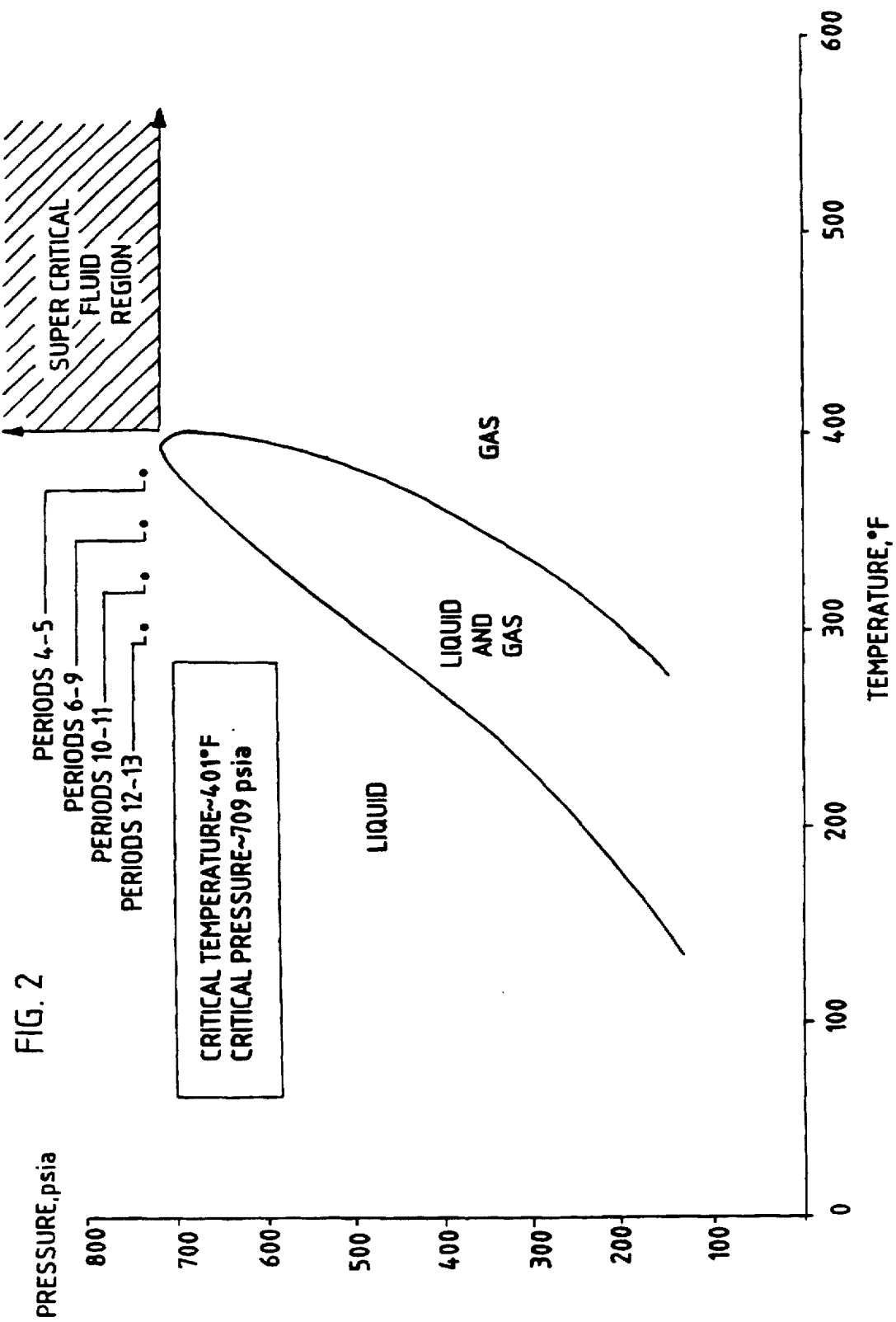

CONVERSION OF AROMATIC AND OLEFINS

This is a continuation of application Ser. No. 08/504,362 filed Jul. 19, 1995 now abandoned.

BACKGROUND OF THE INVENTION

1. Field of the Invention

This invention relates to a process for the alkylation of at least one volatile aromatic compound with at least one aliphatic mono-olefinic alkylating agent and for the concurrent condensation of such alkylating agent, and more particularly relates to the removal of volatile aromatic compounds from a refinery stream or a gasoline blending stock and for the production of gasoline boiling range alkylation and condensation products.

2. Discussion of the Prior Art

It is highly desirable to reduce the level of benzene in gasoline and thus in various refinery streams and gasoline blending stocks. It is well known that alkylation of light aromatics like benzene and toluene in such streams and blending stocks with a light ($C_2$–$C_5$) aliphatic mono-olefinic alkylating agent can result in a significant decrease in the benzene level as well as a significant increase in the octane number of such refinery streams and gasoline blending stocks.

It is also well known that catalytic condensation—or, in other words, oligomerization or polymerization—of the aforesaid mono-olefinic alkylating agent takes place concurrently with the aforesaid alkylation and is extremely useful in converting $C_2$–$C_5$ mono-olefinic hydrocarbons or mixtures thereof into higher molecular weight hydrocarbons of greater economic value. For example, they are used to convert propylene into $C_6$–$C_{12}$ hydrocarbons which are good quality gasoline blending components. Consequently, it is extremely important to effect the desired alkylation without adversely affecting the aforesaid condensation reaction. Since such light mono-olefins are typically available in substantially larger amounts in various refinery streams than are such light aromatics, it is also highly desirable to develop ways to use a relatively high ratio of such light mono-olefins to such light aromatics in such alkylations. However, prior attempts to do so have resulted in coke deposition on, and deactivation of, the solid alkylation catalyst typically employed, excessive condensation of the olefinic alkylating agent and multiple alkylation of the aromatic substrates to form polyalkylated aromatics that boil above the normally accepted gasoline boiling point end points. In addition, in some prior art cases, the alkylation has proceeded to the desired extent, but the concurrent condensation of the mono-olefinic alkylating agent proceeds to a significantly reduced extent.

The alkylation of benzene is widely practiced commercially. For instance, the alkylation of benzene with propylene to form cumene is described in U.S. Pat. Nos. 3,132, 109; 3,293,315; 3,499,826; 3,510,534; 3,520,945 and 4,008, 290. These references also describe solid phosphoric acid (SPA) alkylation catalysts which are commonly employed in this process. Another catalyst system utilizes boron trifluoride to effect the alkylation of benzene with ethylene and propylene. This alkylation process is described in U.S. Pat. Nos. 2,995,611; 3,126,421; 3,238,268 and 3,894,090. A large number of other catalyst systems are known. Examples are found in U.S. Pat. Nos. 2,887,520 and 3,336,410.

Mikulicz et al., U.S. Pat. No. 4,137,274, discloses a process for the production of motor fuel by the polymerization of aliphatic $C_3$ and $C_4$ mono-olefins in the presence of a solid catalyst wherein an undesirable layer of polymers that forms on the surface of the catalyst is removed by passing a small amount of a liquid aromatic hydrocarbon through the polymerization zone. This patent discloses that a broad embodiment of the process disclosed therein comprises admixing about 0.5 to about 5.0 weight percent of an aromatic hydrocarbon having a boiling point below 400° F. into a feed stream comprising normally gaseous aliphatic olefins and contacting the resulting stream with the polymerization-catalyst in a polymerization zone maintained under polymerization conditions. Such polymerization conditions include the use of a pressure that is sufficient to maintain more than 50 volume percent of the aforesaid aromatic hydrocarbon in the liquid phase. A broad range of suitable pressures is disclosed as being from about 50 psig to about 1000 psig, with a preferred pressure range being from 100 to 500 psig.

Herout et al., U.S. Pat. Nos. 4,140,622 and 4,209,383, describe alkylation processes which reduce the benzene content of gasoline streams. Both patents note that high olefin-to-benzene ratios in an alkylation zone promote undesirable side reactions. In particular, U.S. Pat. No. 4,209,383 contains the following statement: "However, a very large excess of the olefin leads to the production of polyalkylated aromatics boiling above the normally accepted gasoline boiling point curve end points."

Nixon, U.S. Pat. No. 3,293,315, and Jones, U.S. Pat. No. 3,527,823, disclose processes for producing mono-alkylated aromatic hydrocarbons by mixed-phase alkylation at low olefin-to-benzene ratios in the presence of solid phosphoric acid catalysts. These patents do not teach high aromatic conversion by alkylation.

Keown et al., U.S. Pat. No. 3,751,504, describes vapor-phase alkylation of benzene and other aromatics conducted in the presence of zeolitic catalyst at a high temperature of 600°–900° F. and with olefin-to-aromatic ratios of 1.0 or substantially less. This patent suggests addition of an alkylating agent in separate streams to individual reactor stages with cooling between reactor stages.

Sato et al., U.S. Pat. No. 4,377,718, discloses that a particular isomer of xylene may be produced by means of a vapor phase methylation of toluene catalyzed by a zeolite if a vapor-phase methylating agent is fed into each of a plurality of series-connected fixed catalyst layers. This patent teaches that the mole ratio of methylating agent to aromatic substrate in any catalyst layer should not exceed 1.0 and that aromatic conversions of 60% or less result.

Inwood et al., U.S. Pat. No. 4,459,426, discloses a process for liquid-phase alkylation in the presence of a zeolite catalyst at olefin-to-aromatic molar ratios which are substantially less than one. This patent suggests that olefins may be injected into a reactor at more than one location in order to maintain a reaction temperature by quenching the heat of reaction.

Harandi et al., U.S. Pat. No. 4,950,823, is directed to a process which comprises an integrated product recovery system for a primary catalytic hydrocarbon reforming reactor and a secondary catalytic olefins oligomerization-alkylation reactor. This patent suggests one method of upgrading benzene-rich reformate by means of oligomerization and alkylation.

Sachtler et al., U.S. Pat. No. 5,120,890, discusses the aforesaid disclosures of U.S. Pat. Nos. 3,132,109; 3,293, 315; 3,527,823; 3,751,504; 4,140,622; 4,209,383; 4,377, 718; 4,459,426; 4,922,053 and 4,950,823 in its columns 1 and 2 and concludes in column 2, lines 23–29 that "[a]ll of the prior art processes referenced above utilize relatively low alkylating agent to aromatic molar ratios which necessarily result in low aromatic conversions. The present invention is distinguishable in that it employs relatively high aromatic conversions, while maintaining good aromatic alkylation selectivity."

U.S. Pat. No. 5,120,890 discloses the injection of the mono-olefinic alkylating agent through a multiplicity of injection points uniquely spaced between the inlet and outlet of the alkylation zone. More particularly, this patent discloses that no more than 90 volume percent of the solid alkylation catalyst bed in the alkylation zone is located between any two adjacent injection points or located between the inlet or the outlet and the injection point which is nearest, and no more than 75 mole percent of the total amount of the alkylating agent is injected through each of the injection points. The total amount of the alkylating agent in moles is from about 2.0 to about 5.0 times the total amount of benzene and toluene in moles introduced into the alkylation zone. The alkylation zone is maintained under benzene-alkylation promoting conditions of a temperature of from about 0° C. to about 450° C., preferably from about 150° C. to about 350° C., and a pressure of from about 3 atmospheres to about 80 atmospheres, preferably from about 20 atmospheres to about 70 atmospheres.

U.S. Pat. No. 5,120,890 also states that conducting the alkylation in the liquid phase or supercritical phase is better than in a mixed phase, which in turn is better than in the vapor phase, in order to achieve high benzene conversion. Table 1 in U.S. Pat. No. 5,120,890 illustrates that at molar ratios of olefins-to-light aromatics in the range of 2.2 to 2.4, at pressures in the range of 715–727 psig and at temperatures in the range of 155° C.–190° C., the benzene conversion decreased from about 90 mole percent when the propylene alkylation agent was introduced through three injection points in Periods 1–3, to about 79 mole percent when the propylene alkylating agent was introduced through a single injection point in Periods 6–9. However, the highest benzene conversion resulting from triple injection of the propylene alkylating agent occurs at the expense of the production of undesirable polyalkylated aromatic compounds as evidenced by the substantial increase of the boiling end point of the product relative to that obtained with single point injection of the propylene alkylating agent, for example, 27° F. higher for products produced in Periods 1–3 than for products produced in Periods 6–9. By contrast, the propylene conversion increased from 94–95 mole percent when the propylene alkylating agent was introduced through three injection points in Periods 1–3 to about 98–99 mole percent when the propylene alkylating agent was introduced through a single injection point in Periods 6–9. Furthermore, in Periods 6–9 which were performed at constant temperature, pressure and space velocity, the propylene alkylating agent conversion progressively drops from 96.9 to 95.1% over a span of only 18 hours. This decrease in propylene conversion with time evidences substantial catalyst deactivation.

OBJECTS OF THE INVENTION

It is therefore a general object of the present invention for the catalytic alkylation of a volatile aromatic compound with an aliphatic mono-olefinic alkylating agent and for the concurrent condensation of such alkylating agent.

More particularly, it is an object of the present invention to provide an improved catalytic method for removing volatile aromatic compounds from a refinery stream or a gasoline blending stock by the aforesaid alkylation and for the production by the aforesaid alkylation and condensation of gasoline boiling range alkylation and condensation products.

It is a further object of the present invention to provide an improved aforesaid method in which deactivation of the catalyst is substantially reduced.

It is yet another object of the present invention to provide an improved aforesaid method in which the resulting alkylated aromatic compounds and resulting condensation products boil within the normally accepted gasoline boiling point end points.

It is a further object of the present invention to provide an improved aforesaid method in which the aforesaid alkylation occurs in the presence of a substantial excess of the aforesaid alkylating agent and with the simultaneous introduction of the total amount of the aforesaid aromatic compounds and alkylating agent into the same reaction zone.

Other objects and advantages of the present invention will become apparent upon reading the following detailed description and appended claims.

SUMMARY OF THE INVENTION

These objects are achieved by the process of the present invention for alkylating at least one volatile aromatic compound with an alkylating agent comprising at least one light aliphatic mono-olefin and for concurrently condensing the aforesaid alkylating agent, comprising: introducing the aforesaid alkylating agent and at least one volatile aromatic compound into a reaction zone which contains a solid alkylation- and condensation-promoting catalyst and which is maintained at alkylation- and condensation-promoting conditions of at least the critical temperature of the reactant mixture and at a total pressure that is above the critical pressure of the reactant mixture.

BRIEF DESCRIPTION OF DRAWINGS

FIG. 1 illustrates the envelop of reaction mixture having critical temperature about 353° F. and critical pressure about 744 psia, and FIG. 2 illustrates the envelop of reaction mixture having critical temperature about 401° F. and critical pressure about 709 psi.

DETAILED DESCRIPTION OF THE PREFERRED EMBODIMENTS

Suitable volatile aromatic compounds for alkylation in the method of the present invention comprise at least one of benzene and toluene and preferably comprise both benzene and toluene and more preferably comprise benzene, toluene and a xylene. The source of the aforesaid volatile aromatic compounds is not limited to any particular refinery stream or gasoline blending stock. A suitable source refinery stream or blending stock typically contains about 0.1 to 100 mole percent of benzene. It may also contain various $C_6$ to $C_{10}$ aromatic hydrocarbons. The total concentration of all aromatic hydrocarbons in the source stream may be above 25 mole percent. The source refinery stream or blending stock will also normally contain some $C_4$ to $C_6$ paraffinic hydrocarbons. These may include a butane, n-pentane, isopentane, n-hexane, and isohexane, which will normally be present at a total concentration of above 5.0 mole percent. $C_7$ to $C_9$ paraffinic hydrocarbons such as heptanes and isooctane are also present in many source refinery streams or blending stocks. The total concentration of these $C_7$ to $C_9$ paraffins will normally be above 2.0 mole percent and may be above 15.0 mole percent. The exact composition of the source refinery stream or blending stock will depend on its source. Two typical sources of source refinery streams or blending stocks are bottoms product from a stripper column used in fluid catalytic cracking gas concentration units and stabilized catalytic reformate, especially light reformate fractions, which contain $C_6$ to $C_9$ aromatic hydrocarbons.

A light gasoline stream is a preferred type of source refinery stream for the method of this invention. As used herein, the term "light gasoline stream" is intended to refer to a benzene-containing stream comprising a mixture of aromatic and paraffinic hydrocarbons having boiling points between about 32° C. and 125° C. and which could be used as a major component of gasoline either immediately or after further processing or blending. Light reformate fractions are especially preferred as a source of volatile aromatic compounds for use in the method of this invention.

The light gasoline stream or light reformate fraction which is employed in the method of this invention preferably contains substantially no aromatic hydrocarbons other than benzene, toluene and xylene and preferably contains a high concentration of benzene and toluene. Therefore, the feed stream which will be adapted for use as the light gasoline or light reformate fraction is often prepared by fractional distillation in a fractionation zone maintained under suitable fractionation conditions. Preferably, this zone comprises a single fractionation column which is sized according to well known criteria based on the flow rate and composition of the feed stream The conditions used in this zone may be those which are customary in the art. The criteria for operation of the fractionation zone is that substantially all of the benzene contained in the feed stream is separated into a light gasoline stream or light reformate fraction, which will be the overhead product of the fractionation zone. Toluene may also be present in this light gasoline stream, or, optionally, most of the toluene may be retained in the heavy hydrocarbon stream removed as the bottoms product of this fractionation zone. The overhead product of the zone will also typically contain various $C_4$ to $C_7$ paraffinic hydrocarbons, and possibly some $C_5$ to $C_7$ naphthenes, while substantially all of the $C_8$ to $C_{10}$ aromatic hydrocarbons will be contained in the heavy hydrocarbon stream separated as the bottoms product. The light reformate stream produced by distillation of a full boiling range product of catalytic reforming is an especially preferred source of light gasoline for use in the method of the present invention.

Suitable light aliphatic mono-olefinic alkylating agents for condensation and for alkylation of the aforesaid at least one volatile aromatic compound in the method of this invention are those mono-olefinic molecules that are commonly known in the art to be capable of replacing a hydrogen atom which is bonded to an aromatic carbon atom in a benzene molecule, with the result that an alkyl group becomes permanently attached to the aromatic carbon atom. Examples of suitable alkylating agents are ethylene, propylene, butylenes and amylenes. Preferably the alkylating agent is ethylene, propylene, butylenes, or a mixture thereof. Mixtures which include at least one such alkylating agent and which sometimes includes other compounds, such as at least one paraffin of approximately the same carbon number, for example, ethane, propane, a butane, or a pentane as diluents or impurities, can be employed in the method of the present invention.

A portion or even all of the alkylating agent employed in the method of the present invention may be present initially in the source of the aforesaid volatile aromatic compounds, namely, the source refinery stream or gasoline blending stock, or may be from a separate source which is admixed with the aforesaid volatile aromatic compound upstream of the reactor or within the reactor. In the method of the present invention, the entire amounts of the aforesaid alkylating agent and of the at least one volatile aromatic compound are each introduced into the reaction zone through a single injection point. They can either be introduced as separate streams through separate single injection points or as a combined stream through a single injection point. The aforesaid alkylating agent and aforesaid at least one volatile aromatic compound are introduced into the reaction zone at a mole ratio of at least 2:1, preferably of from about 2:1 to about 20:1, more preferably from about 2:1 to about 15:1, and most preferably from about 3:1 to about 10:1 of the aforesaid alkylating agent-to-the aforesaid at least one volatile aromatic compound.

The reaction zone is maintained under benzene, alkylation- and mono-olefin condensation-promoting conditions. Such conditions include a temperature of at least the critical temperature of the reactant mixture and a total pressure that is above the critical pressure of the reactant mixture. The critical temperature and critical pressure of the reactant mixture are that temperature and pressure above which the gas and liquid phases of the reactant mixture become so alike that they can no longer be distinguished as separate phases. Thus, the critical temperature and critical pressure of the reactant mixture are fundamental properties of a reactant mixture, which depend on the composition of the specific reaction mixture, and can be readily calculated using the Soave-Redlich-Kwong equation of state as is well known in the art. The critical temperatures and critical pressures of the representative components of a typical reactant mixture that is introduced into the reaction zone in the method of the present invention are shown in Table 1 and were obtained from R. C. Reid, J. M. Prausnitz, and T. K. Sherwood, The Properties of Gases and Liquids, McGraw-Hill, New York (1977). Also shown in Table 1 is the mole percent of these components in such reactant mixture introduced into the reactor in the method of this invention. The mole ratio of alkylating agent-to-the aromatic compounds is 3.2:1. The critical temperature, critical pressure and phase envelope of such reactant mixture were determined using the Soave-Redlich-Kwong equation of state. The resulting phase envelope of the reactant mixture is shown in FIG. 1.

TABLE 1

| Component | Critical Temperature (°F.) | Critical Pressure (psia) | Mole % in Reactant Mixture |
|---|---|---|---|
| Propylene | 197 | 670 | 20.6 |
| Propane | 206 | 616 | 12.8 |
| i-Butane | 275 | 529 | 12.4 |
| n-Butane | 306 | 551 | 12.9 |
| trans-2-butene | 312 | 595 | 9.8 |
| 1-butene | 296 | 584 | 4.5 |
| Isobutylene | 293 | 581 | 3.0 |
| Isopentane | 369 | 491 | 2.6 |
| Pentane | 386 | 490 | 2.7 |
| n-Hexane | 454 | 431 | 2.1 |
| Benzene | 552 | 710 | 3.8 |
| Isoheptane | 495 | 397 | 2.4 |
| n-Heptane | 513 | 397 | 2.4 |
| Toluene | 605 | 597 | 7.6 |
| m-xylene | 651 | 515 | 0.5 |

The phase envelop in FIG. 1 illustrates that the critical temperature critical pressure of the reactant mixture of Table 1 are approximately 353° F. and approximately 744 psia, respectively, which are the lowest temperature and pressure that can be employed in the method of the present invention when this particular reactant mixture is employed. Temperatures and pressures in the shaded area in FIG. 1—and higher temperatures and pressures than those in the shaded area—can also be used for such reactant mixture in the method of the present invention. This region of temperatures and pressures is defined as the supercritical fluid region in accordance with G. G. Hoyer, "Extraction with Supercritical Fluids: Why, How, and So What," Chemtech, pp 440–448, July, 1985.

By contrast, from the composition of the reactant mixture employed in Example 1 of the aforesaid U.S. Pat. No. 5,120,890, the critical temperature, critical pressure and phase envelop of such reactant mixture were also determined using the Soave-Redlich-Kwong equation of state. The resulting phase envelop and supercritical fluid region of such reactant mixture are shown in FIG. 2. The phase envelope in FIG. 2 illustrates that the critical temperature and critical pressure of the reactant mixture employed in Example 1 of U.S. Pat. No. 5,120,890 are 401° F. and 709 psia, respectively. Also shown in FIG. 2 are the temperatures and pressures employed in each of Periods 4–13 (involving single point injection of the total amount of propylene) of such Example 1, which illustrate that the highest temperature employed in the reactor zone in Example 1 of U.S. Pat. No. 5,120,890 was only 374° F., which is substantially below the critical temperature—and thus out of the supercritical fluid region—of 401° F. of the reactant mixture employed in such Example 1. In fact, in Example 1 of U.S. Pat. No. 5,120,890, the "[r]eactor pressure was controlled . . . to produce substantially liquid-phase conditions throughout." Thus, Example 1 of U.S. Pat. No. 5,120,890 was not performed in accordance with the method of the present invention.

The reactant mixture stream is brought into intimate contact with a solid catalyst that is effective in catalyzing the aforesaid alkylation and condensation reactions in a reaction zone that is maintained at light aromatic alkylation- and mono-olefin condensation-promoting conditions. The catalyst employed in the reaction zone preferably comprises a fixed bed of solid material. For instance, a crystalline aluminosilicate such as described in U.S. Pat. Nos. 3,751,504; 3,751,506 and 3,755,483 may be employed. Another suitable catalyst system employs a gaseous catalyst promoter which is circulated through a bed of solid carrier particles in the reaction zone. These carrier particles are normally inorganic oxides such as the gamma and theta forms of alumina, silica, boria and various naturally occurring inorganic oxides including clays and diatomaceous earth. The vaporous catalyst promoter is preferably a halogen-containing compound such as boron trifluoride, boron trichloride, hydrogen chloride, carbon tetrachloride, hydrogen fluoride, ammonium fluoride and ammonium chloride. More preferably, the catalyst promoter is boron trifluoride. This catalyst system is further described in U.S. Pat. Nos. 3,126,421; 3,631,122 and 3,894,090.

However, the preferred catalyst for use in the process of the present invention is a solid phosphoric acid (SPA) catalyst. One reason for this preference is its superior selectivity in producing monoalkylated aromatic hydrocarbons from benzene and an aforesaid mono-olefin compared to most other catalyst systems. Polyalkylated products tend to elevate the endpoint of finished gasoline above commercially acceptable values therefor, and polyalkylation is often accompanied by more rapid carbon deposition on, and thus deactivation of, the solid catalyst. Polyalkylation is also objectionable because it unnecessarily consumes olefins.

Suitable solid phosphoric acid catalysts are available commercially. As used herein, the term "SPA catalyst" or its equivalent is intended to refer generically to a solid catalyst which contains as one of its principal raw ingredients an acid of phosphorus such as ortho-, pyro- or metaphosphoric acid. These catalysts are normally formed by mixing the acid with a siliceous solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, infusorial earth and iron compounds including iron oxide have been added to the carrier to increase its strength and hardness. The combination of the carrier and the additives normally comprises about 15–30 weight percent of the catalyst, with the remainder being the phosphoric acid. However, the amount of phosphoric acid used in the manufacture of the catalyst may vary from about 8–80 weight percent of the catalyst as described in U.S. Pat. No. 3,402,130. The amount of the additives may be equal to about 3–20 weight percent of the total carrier material. Further details as to the composition and production of typical SPA catalysts may be obtained from U.S. Pat. Nos. 3,050,472; 3,050,473 and 3,132,109 and from other references. Although SPA catalyst is preferred, the process of the present invention may be utilized with any other conventional solid alkylation catalyst. Other catalysts of choice include mordenite and omega zeolites. Amorphous silica-alumina or clay may also be employed.

It is highly preferred to utilize a catalyst which will tolerate various amounts of unreactive light hydrocarbons. This allows the use of lower purity gas streams. Also, streams which are higher in paraffin or inert gas concentrations may be used to improve reactor temperature control by means of absorbing heat of alkylation reaction. One such gas stream is that produced as the overhead product stream of a stripping column employed in a typical fluid catalytic cracking gas concentration plant. This gas stream may comprise methane, ethane, ethylene, propane, propylene, butane and various butenes. An olefin-rich $C_3$ to $C_4$ stream derived from the stripping column overhead may also be used.

The catalyst is preferably disposed in fixed beds of particles of the catalyst. Either a tubular or chamber-type reactor structure may be used. In a tubular reactor, the catalyst is placed in relatively small diameter tubes which are surrounded by a heat transfer fluid such as a water jacket to remove the heat liberated by the exothermic reaction. Heat removed in this manner can be used to preheat the feed. In a chamber-type reactor, the reactants flow through a series of large diameter catalyst beds. The temperature of the reactants can be further controlled, if necessary or desired, by recycling relatively inert hydrocarbons (propane) which act as a heat sink and/or by the use of a quench between vertically stacked catalyst beds. The quench material is the same as that used as the recycle stream, and both methods of temperature control may be used simultaneously. The different catalyst beds are preferably contained within a single, cylindrical, vertically oriented vessel, and the feed stream preferably enters the top of the reactor. A chamber-type reactor containing about five catalyst beds is preferred. Separate parallel reactors may be used in large process units.

A highly preferred method of practicing the method of this invention is in a polygasoline unit in a refinery in which light aliphatic mono-olefins in the feed to the polygas unit are condensed—or, in other words, oligomerized or polymerized—to form highly branched $C_6$ through $C_{12}$ olefins which have relatively higher octane value and which are collectively known as polygasoline. A polygas unit generally is made up of a number—for example, eight—multitubular reactors, with each such reactor containing hundreds of tubes, each of which is filled with catalyst particles, typically the aforesaid SPA catalyst. Typically the feed to a polygas unit is free of aromatics but does contain light ($C_3$–$C_4$) paraffins which do not react in the polygas unit. Thus, the output of a polygas unit typically is polygasoline which is essentially free of aromatics and $C_3$–$C_4$ paraffins that are sold as liquefied petroleum gas and mixed butanes. The commercial specifications for liquified petroleum gas and mixed butanes generally limit their olefin contents, and therefore olefin conversion has to be nearly complete in the polygas unit. Thus, the introduction of the at least one volatile aromatic compound of polygas unit in accordance with the method of the present invention should not have a deleterious effect on the degree of olefin conversion.

Furthermore, in one embodiment, it is preferred to recycle to the reactor higher di- or trialkylated products which serves to limit the formation of new such higher di- or trialkylated products.

The present invention will be more clearly understood from the following specific examples.

EXAMPLES 1–3

Experiments were conducted in a pilot plant unit which contains a reactor tube that has 0.375-inch inside diameter and is packed with 7.0 grams of UOP's SPA-2 commercial solid phosphoric acid on kieselguhr catalyst crushed to 10–18 mesh. The composition of the fraction comprising the light aliphatic mono-olefinic alkylating agent fed to the reactor was 55 weight percent of propane, 27 weight percent of propylene and 18 weight percent of butenes. In addition, the light aliphatic mono-olefinic alkylating agent feed contained 1500 parts per million by weight of isopropyl alcohol to enhance catalyst activity and stability. The composition of the fraction comprising the volatile aromatic compounds fed to the reactor is presented in Table 2. The mole ratio of light aliphatic mono-olefin alkylating agent-to-volatile aromatic compounds was 4.6:1.

TABLE 2

| Component | Aromatic Feed Composition (weight percent) | | | |
|---|---|---|---|---|
| | Paraffins | Olefins | Naphthenes | Aromatic |
| $C_5$ | 16.2 | 0.2 | 0.4 | — |
| $C_6$ | 19.1 | 0.4 | 0.9 | 9.8 |
| $C_7$ | 12.9 | 1.1 | 0.9 | 31.6 |
| $C_8$ | 1.9 | 0 | 0.4 | 4.1 |

The experimental parameters employed, which simulate those employed in commercial polygas units in refineries, and the experimental results obtained are presented in Table 3.

TABLE 3

| Example No. | 1 | 2 | 3 |
|---|---|---|---|
| Experimental Parameters | | | |
| Temperature (°F.) | 400 | 400 | 400 |
| Pressure (psia) | 515 | 865 | 1215.7 |
| Total LHSV | 2.7 | 2.7 | 2.7 |

TABLE 3-continued

| Example No. | 1 | 2 | 3 |
|---|---|---|---|
| Experimental Results | | | |
| Conversion (mole %) | | | |
| benzene | 82 | 76 | 78 |
| toluene | 89 | 77 | 75 |
| propylene | 84 | 95 | 96 |
| butenes | 70 | 76 | 78 |
| Product Composition (wt. %) | | | |
| $C_5$ | 9 | 9 | 9 |
| $C_6$ | 12 | 13 | 14 |
| $C_7$ | 20 | 22 | 21 |
| $C_8$ | 7 | 8 | 8 |
| $C_9$ | 13 | 16 | 17 |
| $C_{10}$ | 25 | 24 | 23 |
| $C_{11}$ | 9 | 6 | 6 |
| $C_{12}$ | 5 | 2 | 2 |
| ASTM Distillation (°F.) | | | |
| Initial point | 96 | 96 | 108 |
| 10% | 167 | 163 | 176 |
| 30% | 243 | 226 | 236 |
| 50% | 304 | 273 | 278 |
| 70% | 351 | 323 | 325 |
| 90% | 409 | 374 | 372 |
| End point | 460 | 433 | 435 |
| Residue (vol. %) | 1.5 | 1.3 | 1.1 |
| Relative catalyst activity | 0.72 | 0.93 | 1.0 |

The phase envelop for the reactant mixture employed in Examples 1–3 was also determined by the Soave-Redlich-Kwong equation of state and is similar in shape to that shown in FIG. 1, except that the critical temperature and critical pressure of the reactant mixture of Examples 1–3 are 308° F. and 806 psia, respectively. Thus, the temperatures and pressures employed in each of Examples 2 and 3 were in the supercritical fluid region for the reactant mixture employed, and Examples 2 and 3 illustrate the method of this invention. However, Example 1 is a comparative example in which the pressure employed was below the aforesaid critical pressure. The results in Table 3 illustrate that the conversions of propylene and butene in Examples 2 and 3 were substantially higher than in Example 1. Furthermore, even at the high mole ratio of alkylating agent-to-volatile aromatics employed in the method of the present invention, the use of supercritical fluid conditions in Examples 2 and 3 resulted in the formation of a product and having lower ASTM distillation 90 percent points, End Points, and distillation residue and containing substantially smaller amounts of higher boiling $C_{12}$ products which are dialkylated than did the use of the relatively lower pressure in comparative Example 1. In addition, the relative catalyst activities for the conversion of light mono-olefinic alkylating agent were substantially higher in Examples 2 and 3 than in Example 1. In this context, the relative catalyst activity is defined as proportional to In (1/1−x) where x is the fractional conversion of the aforesaid alkylating agent, with the relative catalyst activity in Example 3 being set at one. It was also found that the relative catalyst activity in Example 3 decreased in a substantially linear fashion by only about 5 percent over a period of 200 hours of operation. By contrast, in Example 1 of U.S. Pat. No. 5,120,890, the relative catalyst activity (as defined hereinabove), setting the relative catalyst activity at Period 6 at one, decreased to 0.96, 0.89 and 0.87 in Periods 7, 8 and 9, respectively. Each such Period corresponded to a 6-hour duration or increment. Thus, over only 18 hours of operation the relative catalyst activity decreased approximately 13 percent from Period 6 to Period 9 due to operation below supercritical fluid conditions. A simple linear extrapolation suggests that the relative catalyst activity would have decreased to zero over a similar 200 hour period of operation, despite operation at a substantially lower temperature, which ordinarily should reduce activity loss.

These examples are presented only by way of illustration, and the invention should not be construed as limited thereto. The most advantageous selection of experimental conditions to be used in the method of this invention will depend on the particular volatile aromatic, alkylating agent and catalyst employed.

From the above description, it is apparent that the objects of the present invention have been achieved. While only certain embodiments have been set forth, alternative embodiments and various modifications will be apparent from the above description to those skilled in the art and are considered equivalent and within the spirit and scope of the invention.

Having described the invention, what is claimed is:

1. A process for alkylating at least one volatile aromatic compound with alkylating agent and concurrently condensing alkylating agent, which comprises: introducing at a common point of injection alkylating agent comprising at least one light aliphatic monoolefin and volatile aromatic compound comprising at least one member selected from the group consisting of benxylenes, into a reaction zone which contains a solid alkylation- and condensation-promoting catalyst and is maintained at alkylation- and condensation-promoting conditions which include temperatures of at least the critical temperature of the reactant mixture and total pressure that is above the critical pressure of the reactant mixture, and wherein alkylating agent and volatile aromatic compound are introduced into the reaction zone at a mole ratio of at least about 2:1 of the alkylating agent-to-the volatile aromatic compound.

2. The process of claim 1 wherein the volatile aromatic compound consists substantially of benzene, toluene or both.

3. The process of claim 1 wherein the volatile aromatic compound consists essentially of benzene, toluene, and at least one xylene.

4. The process of claim 1 wherein the volatile aromatic compound is introduced into the reaction zone in a gasoline boiling range product comprising a refinery stream or a gasoline blending stock.

5. The process of claim 1 wherein the alkylating agent comprises propylene, a butylene or mixtures thereof.

6. The process of claim 5 wherein the alkylating agent consists substantially of propylene, a butylene, an amylene or mixtures thereof.

7. The process of claim 5 wherein the alkylating agent consists essentially of ethylene, propylene, a butylene, an amylene or mixtures thereof.

8. The process of claim 1, wherein the alkylating agent and the volatile aromatic compound are introduced into the reaction zone at a mole ratio of from about 2:1 to about 20:1 of the alkylating agent-to-the volatile aromatic compound.

9. The process of claim 1 wherein the aforesaid alkylating agent and the aforesaid at least one volatile aromatic compound are introduced into the reaction zone at a mole ratio of from about 3:1 to about 10:1 of the aforesaid alkylating agent-to-the aforesaid at least one volatile aromatic compound.

10. A process for alkylating at least one volatile aromatic compound with alkylating agent and concurrently condensing alkylating agent, which comprises: introducing at a common point of injection alkylating agent comprising at least one light aliphatic mono-olefin, and volatile aromatic compound comprising at least one member selected from the group consisting of benzene, toluene and xylenes, into a reaction zone which contains a solid alkylation- and condensation-promoting catalyst and is maintained at alkylation- and condensation-promoting conditions which include temperatures of at least the critical temperature of the reactant mixture and total pressure that is above the critical pressure of the reactant mixture, and wherein alkylating agent and volatile aromatic compound are introduced into the reaction zone at a mole ratio of at least about 2:1 to about 20:1 of the alkylating agent-to-the volatile aromatic compound.

11. The process of claim 10 wherein the volatile aromatic compound consists substantially of benzene, toluene or both.

12. The process of claim 10 wherein the volatile aromatic compound consists essentially of benzene, toluene, and at least one xylene.

13. The process of claim 12 wherein the alkylating agent comprises propylene, a butylene or mixtures thereof.

14. The process of claim 12 wherein the alkylating agent consists substantially of propylene, a butylene, an amylene or mixtures thereof.

15. The process of claim 14 wherein the alkylating agent consists essentially of ethylene, propylene, a butylene, an amylene or mixtures thereof.

16. The process of claim 14 wherein the volatile aromatic compound is introduced into the reaction zone in a gasoline boiling range product comprising a refinery stream or a gasoline blending stock.

17. The process of claim 16 wherein the alkylating agent and the volatile aromatic compound are introduced into the reaction zone at a mole ratio of from about 3:1 to about 10:1 of the alkylating agent-to-the volatile aromatic compound.

* * * * *

UNITED STATES PATENT AND TRADEMARK OFFICE
CERTIFICATE OF CORRECTION

PATENT NO.: 5,792,894

DATED: August 11, 1998

INVENTOR(S): George A. Huff, Jr., Robert L. Mehlberg, Peter M. Train

It is certified that error appears in the above-identified patent and that said Letters Patent is hereby corrected as shown below:

| Col. | Line | |
|---|---|---|
| 9 | 65 | (Table 3, Example No. 3, Pressure (psia)) reads "1215.7" should read --1215-- |
| 11 | 27 | reads "consisting of benxylenes, into a"... should read --consisting of benzene, toluene, and xylenes, into a--... |

Signed and Sealed this

Fifth Day of January, 1999

Attest:

Attesting Officer

Acting Commissioner of Patents and Trademarks